(12) United States Patent
Joseph et al.

(10) Patent No.: US 9,181,270 B2
(45) Date of Patent: Nov. 10, 2015

(54) METHOD OF MAKING SULFIDE COMPOUNDS

(71) Applicant: Universal Display Corporation, Ewing, NJ (US)

(72) Inventors: Scott Joseph, Ewing, NJ (US); Chuanjun Xia, Lawrenceville, NJ (US); Alexey Borisovich Dyatkin, Ambler, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

(21) Appl. No.: 14/193,771

(22) Filed: Feb. 28, 2014

(65) Prior Publication Data
US 2015/0246928 A1    Sep. 3, 2015

(51) Int. Cl.
| | |
|---|---|
| *A61K 31/4402* | (2006.01) |
| *A61K 31/506* | (2006.01) |
| *A61K 31/519* | (2006.01) |
| *C07D 495/04* | (2006.01) |
| *C07D 213/70* | (2006.01) |
| *C07D 239/30* | (2006.01) |
| *H01L 51/00* | (2006.01) |

(52) U.S. Cl.
CPC ............ *C07D 495/04* (2013.01); *C07D 213/70* (2013.01); *C07D 239/30* (2013.01); *H01L 51/0067* (2013.01); *H01L 51/0071* (2013.01)

(58) Field of Classification Search
CPC   A61K 31/4402; A61K 31/506; A61K 31/519
See application file for complete search history.

(56) References Cited

U.S. PATENT DOCUMENTS

| | | |
|---|---|---|
| 4,769,292 A | 9/1988 | Tang et al. |
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0175553 A1 | 9/2003 | Thompson et al. |

(Continued)

FOREIGN PATENT DOCUMENTS

| | | | |
|---|---|---|---|
| CN | 102786537 | * 11/2012 | ................ C07F 1/08 |
| EP | 0650955 | 5/1995 | |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

(Continued)

*Primary Examiner* — Erich A Leeser
(74) *Attorney, Agent, or Firm* — Duane Morris LLP

(57) ABSTRACT

According to one embodiment of the present disclosure, a method of making sulfide compounds using Scheme 1

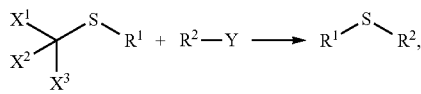

Scheme 1 is disclosed. In Scheme 1, $X^1$, $X^2$, and $X^3$ are independently selected from the group consisting of F, Cl, Br, and I; Y is selected from the group consisting of Cl, Br, and I; and $R^1$ and $R^2$ are independently selected from the group consisting of alkyl, cycloalkyl, alkenyl, cycloalkenyl, alkynyl, cycloalkynyl, alkyl, aryl, and heteroaryl, wherein $R^1$ and $R^2$ may be further substituted, and wherein $R^1$ is optionally covalently linked to $R^2$ and the reaction is intramolecular. In some embodiments, no catalyst is used in Scheme 1.

19 Claims, 1 Drawing Sheet

(56) References Cited

U.S. PATENT DOCUMENTS

| | | |
|---|---|---|
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 1725079 | 11/2006 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1)162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

(56) References Cited

OTHER PUBLICATIONS

Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic LIght-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Senning, Alexander, et al., "Die Umsetzung des Trichlormethylphenylsulfids mit Grignardreagenz," Acta Chem. Scand., 1960, vol. 14, pp. 1444-1445; and English translation.

\* cited by examiner

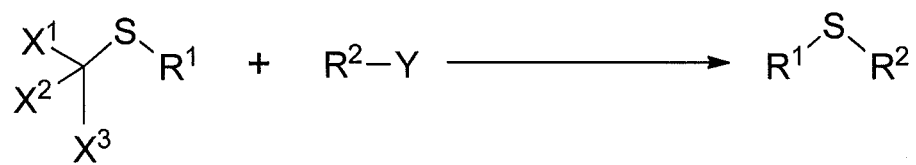
Scheme 1

METHOD OF MAKING SULFIDE COMPOUNDS

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to a method of forming sulfide compounds.

BACKGROUND

Organic compounds containing carbon-sulfur bonds, including, but not limited to, thioethers, have found utility in a broad array of fields, such as pharmaceuticals and organic semiconductors. For example, an array of aryl sulfides are used for diverse clinical applications such as the treatment of Alzheimer's and Parkinson's diseases, treatment of cancer, and treatment of human immunodeficiency virus (HIV) diseases. In addition, dibenzothiophene, azadibenzothiophene, and derivatives thereof, are key building blocks for organic electronic materials used in organic light-emitting devices (OLEDs) and organic field-effect transistors (OFETs). While known techniques can be used to form some of these compounds, the known synthetic techniques are limited in terms of flexibility, yield, or both.

SUMMARY OF THE INVENTION

According to one embodiment of the present disclosure, a method of making sulfide compounds using Scheme 1:

Scheme 1

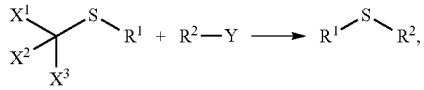

is disclosed. In Scheme 1, $X^1$, $X^2$, and $X^3$ are independently selected from the group consisting of F, Cl, Br, and I; Y is selected from the group consisting of Cl, Br, and I; and $R^1$ and $R^2$ are independently selected from the group consisting of alkyl, cycloalkyl, alkenyl, cycloalkenyl, alkynyl, cycloalkynyl, alkyl, aryl, and heteroaryl, where $R^1$ and $R^2$ may be further substituted, and where $R^1$ is optionally covalently linked to $R^2$ and the reaction is intramolecular. Scheme 1 can be used with or without a catalyst.

BRIEF DESCRIPTION OF THE DRAWINGS

FIG. 1 shows Scheme 1 as disclosed herein.

DETAILED DESCRIPTION

Organic compounds containing carbon-sulfur bonds, including, but not limited to, thioethers, have found utility in a broad array of fields, such as pharmaceuticals and organic semiconductors. For example, an array of aryl sulfides are used for diverse clinical applications such as the treatment of Alzheimer's and Parkinson's diseases, treatment of cancer, and treatment of human immunodeficiency virus (HIV) diseases. In addition, dibenzothiophene, azadibenzothiophene, and derivatives thereof, are key building blocks for organic electronic materials used in organic light-emitting devices (OLEDs) and organic field-effect transistors (OFETs). While known techniques can be used to form some of these compounds, the known synthetic techniques are limited in terms of flexibility, yield, or both.

According to one embodiment of the present disclosure, a method of making sulfide compounds using Scheme 1:

Scheme 1

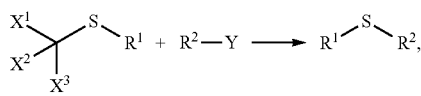

is disclosed. In Scheme 1, $X^1$, $X^2$, and $X^3$ are independently selected from the group consisting of F, Cl, Br, and I; Y is selected from the group consisting of Cl, Br, and I; and $R^1$ and $R^2$ are independently selected from the group consisting of alkyl, cycloalkyl, alkenyl, cycloalkenyl, alkynyl, cycloalkynyl, alkyl, aryl, and heteroaryl, wherein $R^1$ and $R^2$ may be further substituted, and wherein $R^1$ is optionally covalently linked to $R^2$ and the reaction is intramolecular. In some embodiments, no catalyst is used in Scheme 1.

The term "halo" or "halogen" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. naphthyl, dibenzofuryl) or as if it were the whole molecule (e.g. naphthalene, dibenzofuran). As used herein, these different ways of designating a substituent or attached fragment are considered to be equivalent.

In some embodiments of the present disclosure, $R^1$ and $R^2$ can be further substituted by hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In some embodiments, $R^1$, $R^2$, or both can be an alkyl selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, and combinations thereof.

In some embodiments, $R^1$ and $R^2$ are independently selected from the group consisting of aryl, substituted aryl, heteroaryl, and substituted heteroaryl. In some more specific embodiments, $R^1$ and $R^2$ are independently selected from the group consisting of phenyl, substituted phenyl, pyridyl, substituted pyridyl, pyrimidyl, and substituted pyrimidyl. In still other embodiments, $R^2$ is pyridyl, substituted pyridyl, pyrimidyl, and substituted pyrimidyl, with a N heteroatom ortho to Y.

In some embodiments, at least one of $R^1$ and $R^2$ is heteroaryl comprising one or more N atoms. In some embodiments, at least one of $R^1$ and $R^2$ is heteroaryl containing only N heteroatoms. In some embodiments, $R^2$ is heteroaryl with an N heteroatom ortho to Y.

In some embodiments, $X^1$, $X^2$, and $X^3$ are Cl. In some embodiments, Y is Cl or Br. In other embodiments, $X^1$, $X^2$, and $X^3$ are Cl, and Y is Cl or Br.

In some embodiments, $R^1$ is covalently linked to $R^2$ and the reaction is intramolecular. In such embodiments, the product of Scheme 1 can be a closed ring that includes the S of the $R^1$—S—$R^2$ moiety. In some embodiments, $R^1$ and $R^2$ are covalently bonded to one another and the reaction is intramolecular. In still other embodiments, $R^1$ is not covalently linked to $R^2$.

In some embodiments, Scheme 1 can also include a catalyst selected from the group consisting of transition metal complexes. In some embodiments, the transition metal complex can include at least one metal precursor or ligand. In some embodiments, the transition metal complex is formed in situ during the reaction of Scheme 1. In some embodiments, the transition metal complex catalyst can include at least one transition metal selected from the group consisting of Cu, Pd, Ni, Pt, Rh, Ru, Os, Ag, Zn, Ir, Au and Co.

In some embodiments, the reaction occurs in a solvent. Appropriate solvents include, but are not limited to, formamide, tetrahydrofuran, dimethylformamide, dioxane, N,N-dimethylacetamide, N-methyl-2-pyrrolidone, hexamethylphosphoramide, water, and combinations thereof.

In some embodiments, Scheme 1 can include heating the reaction mixture to a temperature of 40° C. or greater. In some embodiments, Scheme 1 can include heating the reaction mixture to a temperature of 50° C. or greater, or 60° C. or greater, or 70° C. or greater. In some embodiments, the heating can last for at least 1 hour, or at least 2 hours, or at least 3 hours, or at least 4 hours.

In some embodiments, product is provided in a yield of greater than 30%. In some embodiments, the product is provided in a yield of greater than 40%, or greater than 50%, or greater than 55%, or greater than 60%.

EXPERIMENTAL

Synthesis of 2-((4-bromophenyl)thio)pyridine

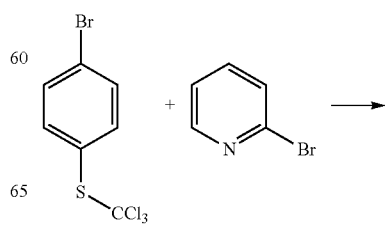

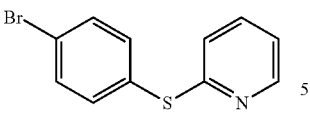

A solution of (4-bromophenyl)(trichloromethyl)sulfane (0.25 g, 0.816 mmol) in 12 mL of formamide was degassed with nitrogen and treated with 2-bromopyridine (0.078 ml, 0.816 mmol). The reaction solution was heated at 75° C. overnight. Then it was cooled to room temperature and diluted with water, extracted with DCM, dried over sodium sulfate, filtered and concentrated. The crude product was purified by column chromatography on silica gel, eluted with 1-5% of EtOAc in 20% DCM/heptanes (v/v), affording 0.14 g (65% yield) of 2-((4-bromophenyl)thio)pyridine.

Synthesis of 2-(phenylthio)pyridine

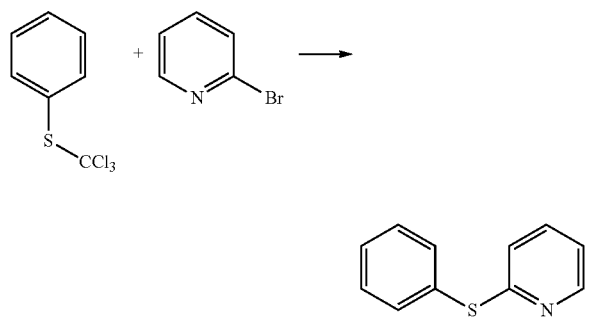

A solution of phenyl(trichloromethyl)sulfane (0.25 g, 1.099 mmol) in formamide (16.40 ml), was degassed with nitrogen and treated with 2-bromopyridine (0.115 ml, 1.209 mmol). The reaction solution was heated at 75° C. overnight. Gas Chromatography-Mass Spectrometry (GCMS) indicates a yield of 81% of 2-(phenylthio)pyridine, and a 7% byproduct of disulfide.

Synthesis of 2-(phenylthio)pyridine

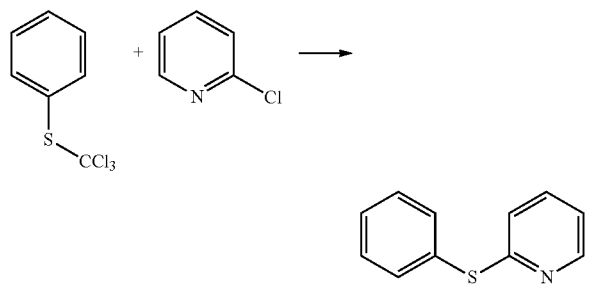

A solution of phenyl(trichloromethyl)sulfane (0.25 g, 1.099 mmol) in formamide (16.40 ml) was degassed with nitrogen and treated with 2-chloropyridine (0.114 ml, 1.209 mmol). The reaction solution was heated at 75° C. overnight. GCMS indicates a yield of 62% of 2-(phenylthio)pyridine, and a 22% byproduct of disulfide.

Synthesis of 2,4-dichloro-5-(2-(methylthio)phenyl)pyrimidine

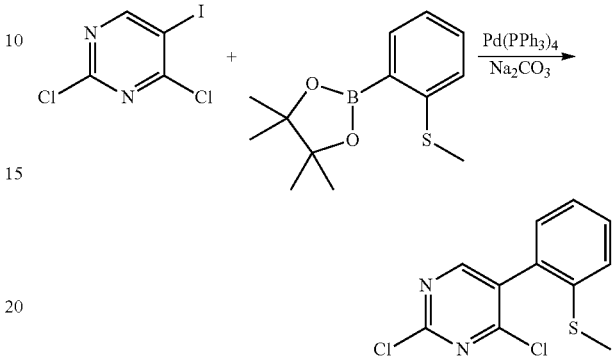

A solution of 2,4-dichloro-5-iodopyrimidine (50.15 g, 182 mmol), 4,4,5,5-tetramethyl-2-(2-(methylthio)phenyl)-1,3,2-dioxaborolane (47.9 g, 192 mmol) in THF (1368 ml) and water (456 ml) was degassed with nitrogen. $Pd(PPh_3)_4$ (10.54 g, 9.12 mmol) was added and degassing continued for several minutes. The mixture was then heated to reflux at 70° C. overnight. After 24 hrs the reaction was cooled to room temperature, the aqueous layer was removed, and the organic layer was washed with brine. The aqueous layer was extracted once with EtOAc, and the combined organic layers were dried over sodium sulfate, filtered and concentrated. The crude material was purified by column chromatography in 10-15% DCM 1-2% EtOAc/heptanes (v/v/v). The product was further purified by dissolving in EtOH and precipitating with heptanes, yielding 35.5 g (72% yield) of 2,4-dichloro-5-(2-(methylthio)phenyl)pyrimidine as white solids.

Synthesis of 2,4-dichloro-5-(2-((trichloromethyl)thio)phenyl)pyrimidine

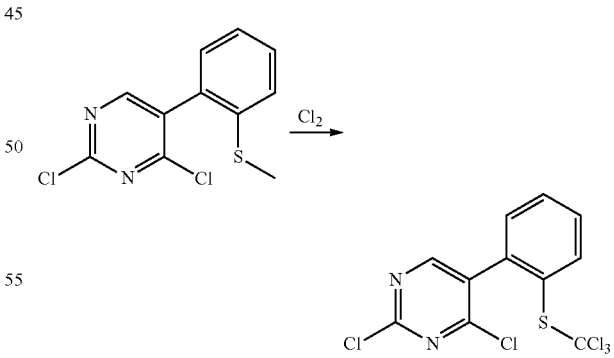

A 2-neck 250 mL round bottom flask was equipped with a gas inlet adapter and a gas outlet attached to two traps in series, the first trap being empty and the second trap containing water. The reaction vessel was charged with 2,4-dichloro-5-(2-(methylthio)phenyl)pyrimidine and carbon tetrachloride (49.8 ml) and heated to reflux to dissolve the 2,4-dichloro-5-(2-(methylthio)phenyl)pyrimidine, then cooled to room temperature creating a clear colorless solution. Chlorine gas was bubbled through the reaction solution while stirring vigorously creating a clear yellow solution. The reaction was monitored by direct NMR of aliquots diluted in DMSO-d6. Upon completion the reaction solution was concentrated in vacuo yielding 14.7 g (99% yield) of 2,4-dichloro-5-(2-((trichloromethyl)thio)phenyl)pyrimidine as yellow solids.

Synthesis of 2-chlorobenzo[4,5]thieno[2,3]dipyrimidine

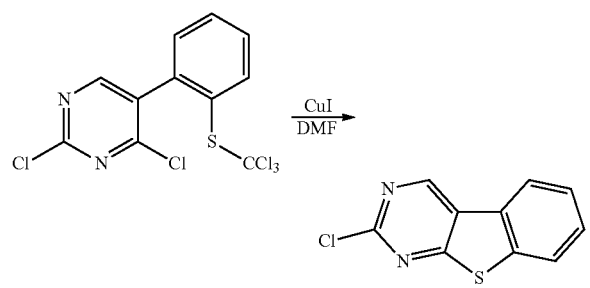

A solution of 2,4-dichloro-5-(2-((trichloromethyl)thio)phenyl)pyrimidine (0.618 g, 1.650 mmol) and copper(I) iodide (0.031 g, 0.165 mmol) in DMF (24.63 ml) was degassed with nitrogen and heated at 110° C. overnight. The reaction solution was cooled to room temperature, diluted with water and filtered. The resulting brown solids were washed with water and a small volume of EtOH. The aqueous layer was extracted twice with EtOAc, combined with the solids, and concentrated in vacuo. The crude product was purified by column chromatography on silica gel, eluted with 10-20% EtOAc/heptanes (v/v), affording 0.14 g (38% yield) of the 2-chlorobenzo[4,5]thieno[2,3-d]pyrimidine as white solids.

Synthesis of 2-chlorobenzo[4,5]thieno[2,3-d]pyrimidine

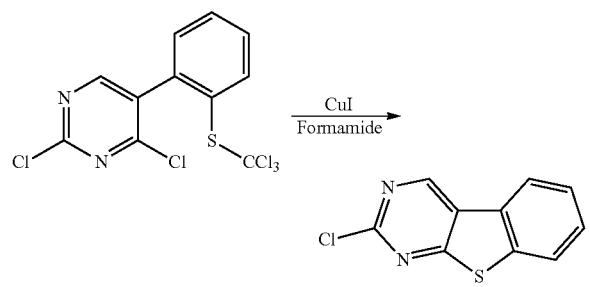

A solution of 2,4-dichloro-5-(2-((trichloromethyl)thio)phenyl)pyrimidine (0.76 g, 2.029 mmol) and copper(I) iodide (0.077 g, 0.406 mmol), in formamide (30.3 ml) was degassed with nitrogen and heated at 60° C. overnight. The solution was then cooled to room temperature, diluted with water, filtered, and washed with a small volume of EtOH to remove disulfide, yielding 0.28 g of white solids. The filtrate slowly crystallized affording 0.03 g of additional product as colorless, crystalline needles. Combined batches provided 0.31 g (69% yield) of 2-chlorobenzo[4,5]thieno[2,3-d]pyrimidine as white solid.

Synthesis of 2-chlorobenzo[4,5]thieno[2,3]pyrimidine

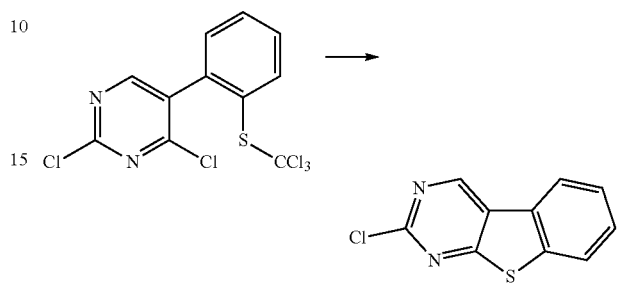

A solution of 2,4-dichloro-5-(2-((trichloromethyl)thio)phenyl)pyrimidine (12.5 g, 33.4 mmol) in formamide (498 ml) was degassed with nitrogen and heated at 60° C. overnight. The reaction solution was cooled to room temperature, diluted with water, filtered and washed with water and a small amount of cold ethanol. White precipitate was recrystallized from EtOH to afford 5.0 g (68% yield) of 2-chlorobenzo[4,5]thieno[2,3-d]pyrimidine as white needles.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A method comprising Scheme 1:

Scheme 1

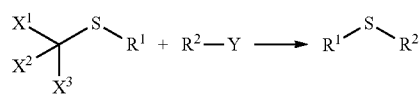

Wherein:
X$^1$, X$^2$, and X$^3$ are independently selected from the group consisting of F, Cl, Br, and I; Y is sleeted from the group consisting of Cl, Br, and I; and R$^1$ and R$^2$ are independently selected from the group consisting of alkyl, cycloalkyl, alkenyl, cycloalkenyl, alkynyl, cycloalkynyl, alkyl, aryl, and heteroaryl, wherein R$^1$ and R$^2$ may be further substituted, and wherein R$^1$ is optionally covalently linked to R$^2$ and the reaction is intramolecular, wherein at least one of R$^1$ and R$^2$ is heteroaryl containing only N heteroatoms.

2. The method of claim 1, wherein R$^1$ and R$^2$ are independently selected from the group consisting of aryl, substituted aryl, heteroaryl, and substituted heteroaryl.

3. The method of claim 2, wherein R$^2$ is heteroaryl with a N heteroatom ortho to Y.

4. The method of claim 1, wherein $R^2$ is heteroaryl with a N heteroatom ortho to Y.

5. The method of claim 1, wherein $R^1$ and $R^2$ are independently selected from the group consisting of phenyl, substituted phenyl, pyridyl, substituted pyridyl, pyrimidyl, and substituted pyrimidyl.

6. The method of claim 1, wherein $R^2$ is pyridyl, substituted pyridyl, pyrimidyl, and substituted pyrimidyl, with a N heteroatom ortho to Y.

7. The method of claim 1, wherein $X^1$, $X^2$, and $X^3$ are Cl.

8. The method of claim 1, wherein Y is Cl or Br.

9. The method of claim 1, wherein $X^1$, $X^2$, and $X^3$ are Cl, and Y is Cl or Br.

10. The method of claim 1, wherein $R^1$ is covalently linked to $R^2$ and the reaction is intramolecular.

11. The method of claim 1, wherein $R^1$ is not covalently linked to $R^2$.

12. The method of claim 1, further comprising a catalyst selected from the group consisting of transition metal complexes.

13. The method of claim 12, wherein said transition metal complex comprises at least one metal precursor or ligand.

14. The method of claim 12, wherein said transition metal complex is formed in situ.

15. The method of claim 12, wherein the catalyst comprises at least one transition metal selected from the group consisting of Cu, Pd, Ni, Pt, Rh, Ru, Os, Ag, Zn, Ir, Au and Co.

16. The method of claim 1, wherein no catalyst is used in Scheme 1.

17. The method of claim 1, wherein the product is provided in a yield of greater than 30%.

18. The method of claim 1, wherein the product is provided in a yield of greater than 40%.

19. The method of claim 1, wherein one of $R^1$ and $R^2$ is alkyl selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, and combinations thereof.

\* \* \* \* \*